United States Patent [19]

Maienfisch et al.

[11] Patent Number: 5,179,121

[45] Date of Patent: Jan. 12, 1993

[54] THIOBUTYRIC ACID DERIVATIVES

[75] Inventors: Peter Maienfisch, Rodersdorf, Switzerland; Manfred Böger, Weil am Rhein, Fed. Rep. of Germany; Eginhard Steiner, Füllinsdorf, Switzerland

[73] Assignee: Ciba-Geigy Corporation, Ardsley, N.Y.

[21] Appl. No.: 745,567

[22] Filed: Aug. 15, 1991

[30] Foreign Application Priority Data

Aug. 21, 1990 [CH] Switzerland .................. 2708/90

[51] Int. Cl.$^5$ .................. A01N 43/06; A01N 37/00; C07C 327/00; C07D 333/32
[52] U.S. Cl. .................. 514/445; 558/250; 558/257; 558/252; 558/253; 558/254; 558/255; 558/256; 514/513; 514/460; 549/66; 549/479
[58] Field of Search .............. 558/250, 257, 252, 253, 558/254, 255, 256; 514/513, 445, 460; 549/66, 479

[56] References Cited

U.S. PATENT DOCUMENTS

| | | | |
|---|---|---|---|
| 3,324,163 | 6/1967 | Hauptchein | 558/250 |
| 4,075,237 | 2/1978 | Kleiner et al. | 558/250 |
| 4,950,666 | 8/1990 | Peake | 514/227 |

FOREIGN PATENT DOCUMENTS

| | | | |
|---|---|---|---|
| 0002206 | 8/1979 | European Pat. Off. | 558/250 |
| 0078562 | 5/1983 | European Pat. Off. | 558/250 |
| 1518781 | 6/1969 | Fed. Rep. of Germany | 558/250 |

OTHER PUBLICATIONS

Helv. Chim. A. 63, 1947–57 (1980).

*Primary Examiner*—Mary C. Lee
*Assistant Examiner*—Robert C. Whittenbaugh
*Attorney, Agent, or Firm*—Kevin T. Mansfield; Edward McC. Roberts

[57] ABSTRACT

Novel 4-chloro-4,4-difluorothiobutyric acid derivatives of the formula I

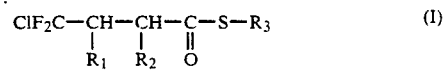

in which $R_1$ and $R_2$ are, independently of one another, hydrogen, $C_1$–$C_4$alkyl or $C_1$–$C_4$halogenoalkyl and $R_3$ is hydrogen or an organic radical can be employed as pest-control agents. Control of insects and arachnids is possible and preferable.

8 Claims, No Drawings

THIOBUTYRIC ACID DERIVATIVES

The present invention relates to novel derivatives of 4-chloro-4,4-difluorothiobutyric acid, processes and intermediates for the preparation thereof, pesticides which contain these compounds, and the use thereof for controlling pests.

The 4-chloro-4,4-difluorothiobutyric acid derivatives according to the invention correspond to the formula I

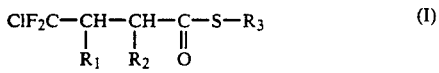

in which $R_1$ and $R_2$ are, independently of one another, hydrogen, $C_1$–$C_4$alkyl or $C_1$–$C_4$halogenoalkyl, and $R_3$ is hydrogen or an organic radical.

The class of polyhalogenated butyryl chlorides is known from the literature as intermediates for pyrethroid haloketones from Helv. Chim. Acta 63, p. 1947-1957 (1980).

The organic radical mentioned in the definition of $R_3$ is any desired organic radical which can be linked in the form of a mercaptan to the carbonyl group of the 4-chloro-4,4-difluorobutyric acid. This entails the mercaptan functionality of this organic radical being linked to a carbon atom. Hence the radical $R_3$ is preferably linked via a carbon atom to the —CO—S— group. Examples representing $R_3$ in each case are substituted or unsubstituted $C_1$–$C_{20}$alkyl, $C_3$–$C_6$cycloalkyl, $C_3$–$C_{10}$alkenyl, benzyl or aryl. $R_3$ is preferably is within the scope of the present invention $C_1$–$C_{20}$alkyl, $C_3$–$C_6$cycloalkyl, $C_3$–$C_{10}$alkenyl, aryl, $C_3$–$C_{10}$halogenoalkenyl; $C_3$–$C_6$cycloalkyl substituted by halogen; aryl substituted by halogen, $C_1$–$C_4$alkyl, $C_1$–$C_4$halogenoalkyl, $C_1$–$C_4$alkoxy, $C_1$–$C_4$halogenoalkoxy, $C_1$–$C_6$alkoxycarbonyl, $C_1$–$C_4$alkylthio or nitro; or $C_1$–$C_{20}$alkyl substituted by halogen, di-$C_1$–$C_4$alkylamino, $C_1$–$C_4$alkoxy, $C_1$–$C_4$alkylthio, $C_1$–$C_{20}$alkoxycarbonyl, $C_3$–$C_7$cycloalkoxycarbonyl, $C_1$–$C_4$alkylcarbonyloxy, $C_3$–$C_6$cycloalkyl, aryl, $C_1$–$C_{10}$alkylaminocarbonyl or anilinocarbonyl; where the aryl groups can each be substituted by halogen, $C_1$–$C_4$alkyl, $C_1$–$C_4$halogenoalkyl, $C_1$–$C_4$alkoxy, $C_1$–$C_4$halogenoalkoxy, $C_1$–$C_4$alkylthio or nitro.

The individual generic terms in the definition of the formula I according to the invention are to be understood as follows:

The halogen atoms suitable as substituents are both fluorine and chlorine, and bromine and iodine, where fluorine, chlorine and bromine are preferred. Halogen is to be understood in this connection as independent substituent or as part of a substituent such as in halogenoalkyl, halogenoalkoxy or halogenophenoxy.

The alkyl, alkylthio and alkoxy radicals suitable as substituents can be straight-chain or branched. Examples of such alkyls which may be mentioned are methyl, ethyl, propyl, isopropyl, butyl, i-butyl, sec-butyl, tert-butyl or pentyl, hexyl, octyl, decyl, dodecyl and isomers thereof. Suitable alkoxy radicals which may be mentioned are, inter alia: methoxy, ethoxy, propoxy, isopropoxy or butoxy and isomers thereof. Alkylthio represents, for example, methylthio, ethylthio, isopropylthio, propylthio or the butylthio isomers.

If the alkyl, alkoxy, alkenyl or aryl groups suitable as substituents are substituted by halogen, they can be only partially or else perhalogenated. The abovementioned definitions apply in this connection to halogen, alkyl and alkoxy. Examples of the alkyl elements in these groups are methyl substituted once to three times by fluorine, chlorine and/or bromine, such as, for example, $CHF_2$ or $CF_3$; ethyl substituted once to five times by fluorine, chlorine and/or bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted once to seven times by fluorine, chlorine and/or bromine, such as, for example, $CH_2CHBrCH_2Br$, $CF_2CHFCF_3$, $CH_2CF_2CF_3$ or $CH(CF_3)_2$; butyl or one of its isomers, substituted once to nine times by fluorine, chlorine and/or bromine, such as, for example, $CF(CF_3)CHFCF_3$ or $CH_2(CF_2)_2CF_3$.

If the alkyl, cycloalkyl or aryl groups defined under $R_3$ are substituted by other substituents, they can be substituted once or more than once by identical or different substituents among those listed. It is preferable for one or two further substituents to be present in the substituted groups.

Examples of cycloalkyl radicals suitable as substituents are cyclopropyl, cyclobutyl, cyclopentyl or cyclohexyl.

Alkenyl groups contain one or more, preferably not more than three, unsaturated carbon-carbon bonds. The double bonds are separated from the linkage point to the sulfur atom by at least one saturated carbon atom. Typical representatives are allyl, methallyl, 2-butenyl or 3-butenyl.

Aryl represents an aromatic hydrocarbon radical or an aromatic heterocyclic radical such as furanyl or thienyl. Aryl preferably means phenyl or naphthyl.

Examples of alkoxycarbonyl radicals are methoxycarbonyl, ethoxycarbonyl, propoxycarbonyl, isopropoxycarbonyl or butoxycarbonyl. Alkylcarbonyl represents, for example, acetyl, propionyl, butyryl or valeryl, and isomers thereof. Alkylcarbonyloxy represents, for example, acetoxy, propionyloxy or butyryloxy.

Examples of cycloalkoxycarbonyl are cyclopropoxycarbonyl, cyclopentyloxycarbonyl, cyclohexyloxycarbonyl or cycloheptyloxycarbonyl.

Aryl groups, especially phenyl nuclei, can carry further substituents, for example each up to three radicals from the group comprising halogen, alkyl, halogenoalkyl and alkoxy or each one or two substituents from the group comprising nitro, halogenoalkoxy, alkylthio and cycloalkyl. The total number of substituents on the phenyl ring together is as a rule not larger than four. It is preferable for these phenyl groups to carry not more than 3 substituents from the series comprising chlorine, bromine, methyl, ethyl and trifluoromethyl.

Among the compounds of the formula I, those subgroups are to be emphasised in which either a) $R_1$ and $R_2$ are, independently of one another, hydrogen, or b) $R_3$ represents $C_1$–$C_{20}$alkyl, $C_3$–$C_6$cycloalkyl, $C_3$–$C_{10}$alkenyl, phenyl, naphthyl, $C_3$–$C_{10}$halogenoalkenyl; $C_3$–$C_6$cycloalkyl substituted by fluorine, chlorine or bromine; phenyl substituted by fluorine, chlorine, bromine, $C_1$–$C_3$alkyl, $C_1$–$C_3$halogenoalkyl, $C_1$–$C_3$alkoxy, $C_1$–$C_3$halogenoalkoxy, $C_1$–$C_4$alkoxycarbonyl, $C_1$–$C_3$alkylthio or nitro, or $C_1$–$C_{20}$alkyl substituted by fluorine, chlorine, bromine, di-$C_1$–$C_4$alkylamino, $C_1$–$C_4$alkoxy, $C_1$–$C_4$alkylthio, $C_1$–$C_{20}$alkoxycarbonyl, $C_3$–$C_7$cycloalkoxycarbonyl, $C_1$–$C_4$alkylcarbonyloxy, $C_3$–$C_6$cycloalkyl, phenyl, $C_1$–$C_{10}$alkylaminocarbonyl or anilinocarbonyl, where the phenyl groups can each be substituted by fluorine, chlorine, bromine, $C_1$-$C_3$alkyl, $C_1$-$C_3$halogenoalkyl, $C_1$-$C_3$alkoxy, $C_1$-$C_3$halogenoalkoxy, $C_1$-$C_3$alkylthio or nitro.

To be emphasised in subgroup b) of the compounds of the formula I are, on the one hand, those in which $R_3$ is phenyl, benzyl, or phenyl or benzyl which is substituted in each case by fluorine, chlorine, bromine, $C_1$-$C_3$alkyl, $C_1$-$C_3$halogenoalkyl, $C_1$-$C_3$alkoxy, $C_1$-$C_4$alkoxycarbonyl, $C_1$-$C_3$halogenoalkoxy, $C_1$-$C_3$alkylthio or nitro. In turn, preferred compounds among these are those in which $R_1$ and $R_2$ are, independently of one another, hydrogen.

On the other hand, among subgroup b) of the compounds of the formula I also to be particularly emphasised are those in which $R_3$ is $C_1$-$C_{12}$alkyl or $C_1$-$C_{12}$alkyl substituted by hydroxyl, fluorine, chlorine, bromine, dimethylamino, methoxy, ethoxy, methylthio, ethylthio, cyclopropyl, cyclopentyl, cyclohexyl or phenyl, where the phenyl radical can in each case be substituted by fluorine, chlorine, bromine, methyl, methoxy, trifluoromethyl, trifluoromethoxy or nitro. The compounds preferred from this group are those in which $R_1$ and $R_2$ are, independently of one another, hydrogen.

Preferred single compounds of the formula I to be mentioned are:
S-benzyl 4-chloro-4,4-difluorothiobutyrate
S-phenyl 4-chloro-4,4-difluorothiobutyrate
S-(4-toluyl) 4-chloro-4,4-difluorothiobutyrate and
S-(3-chlorophenyl) 4-chloro-4,4-difluorothiobutyrate.

The compounds of the formula I according to the invention can be prepared in analogy to known processes. For example, the compound of the formula I is obtained by either a) reacting a 4-chloro-4,4-difluorobutyryl halide of the formula II

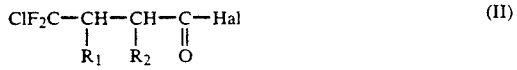

in which $R_1$ and $R_2$ have the meanings given under formula I, and Hal is halogen, preferably chlorine or bromine, preferably in the presence of a base with a mercaptan of the formula III

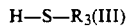

in which $R_3$ has the meaning given under formula I, or b) reacting a 4-chloro-4,4-difluorobutyric acid of the formula IV

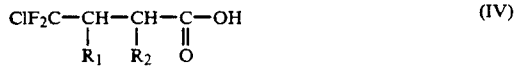

in which $R_1$ and $R_2$ have the meanings given under formula I, in the presence of a water-eliminating agent with a mercaptan of the formula III.

The reaction of process a) (II+III→I) preferably takes place in an inert solvent without hydroxyl groups, in the presence of an organic base such as, for example, an amine such as pyridine, 4-dimethylaminopyridine, lutidine, collidine, trialkylamine, N,N-dialkylaniline or a bicyclic, non-nucleophilic base such as 1,4-diazabicyclo[2.2.2]octane (DABCO), 1,5-diazabicyclo[4.3.0]non-5-ene (DBN) or 1,8-diazabicyclo[5.4.0]undec-7-ene (1.5-5) (DBU). The reaction is generally carried out at temperatures from −30° to +120° C., preferably from −10° to +80° C. In this connection it is expediently carried out in the presence of a solvent or mixture of solvents inert to the reaction. Suitable examples for this purpose are aliphatic and aromatic hydrocarbons such as benzene, toluene, xylenes, petroleum ether, hexane; halogenated hydrocarbons such as chlorobenzene, methylene chloride, ethylene chloride, chloroform, tetrachloromethane, tetrachloroethylene; ethers and ether-like compounds such as dialkyl ethers (diethyl ether, diisopropyl ether, tert-butyl methyl ether etc), anisole, dioxane, tetrahydrofuran; nitriles such as acetonitrile, propionitrile; esters such as ethyl acetate (acetic acid ethyl ester), propyl acetate or butyl acetate; ketones such as acetone, diethyl ketone, methyl ethyl ketone; compounds such as dimethyl sulfoxide (DMSO), dimethylformamide (DMF) and mixtures of such solvents with one another. However, the reaction can also be carried out in an excess of one of the abovementioned bases.

The reaction in process variant b) (IV+III→I) is advantageously carried out in the presence of reagents which eliminate water and activate the carbonyl functionality and are customary for esterifications of thiocarboxylic acids, such as, for example, in the presence of a phosphorus-containing acid derivative such as diethyl cyanophosphonate, diphenyl azidophosphate, diethyl chlorophosphate or diphenylphosphinic chloride, of a urea derivative such as N,N'-carbonyldiimidazole or N,N'-carbonyldi-1,2,4-triazole or of a 1-alkyl-2-halogeno-pyridinium salt such as 1-methyl-2-chloropyridinium iodide or 1-methyl-2-fluoropyridinium iodide. This is expediently carried out in the presence of a solvent or mixture of solvents inert to the reaction, at temperatures from −30° C. to +120° C., preferably −10° C. to +80° C. It is often also carried out in the presence of a base such as, for example, in the presence of an organic amine such as a trialkylamine (trimethylamine, triethylamine, tripropylamine or diisopropylethylamine), a pyridine (pyridine itself, 4-dimethylaminopyridine or 4-pyrrolidinopyridine), a morpholine (N-methylmorpholine) or an N,N-dialkylaniline (N,N-dimethylaniline or N-methyl-N-ethylaniline) or one of the bases mentioned in variant a). Examples of suitable solvents are aliphatic and aromatic hydrocarbons such as benzene, toluene, xylenes, petroleum ether, hexane; halogenated hydrocarbons such as chlorobenzene, methylene chloride, ethylene chloride, chloroform, tetrachloromethane, tetrachloroethylene; ethers and ether-like compounds such as dialkyl ethers (diethyl ether, diisopropyl ether, tert-butyl methyl ether etc), anisole, dioxane, tetrahydrofuran; nitriles such as acetonitrile, propionitrile; esters such as ethyl acetate (acetic acid ethyl ester), propyl acetate or butyl acetate; and mixtures of such solvents with one another.

The various derivatives of the formula I can in principle also be obtained from transesterification from the readily accessible lower alkyl esters of 4-chloro-4,4-difluorobutyric acid.

For example, the derivatives of the formula I can be obtained by base-catalysed transesterification of the lower alkyl esters of the formula V

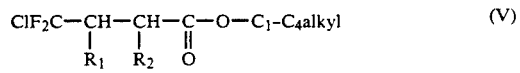

with the mercaptans of the formula III $$H-S-R_3 \quad (III)$$

in which $R_3$ has the meaning given under formula I. In the base-catalysed transesterification, preferably used as base are the sodium or potassium salts of the mercaptan of the formula III, which can be obtained from III, for example, by adding sodium hydride or potassium hydride. The transesterification reaction is preferably carried out at temperatures between $-20°$ C. and $+120°$ C., in particular between $-10°$ C. and $+80°$ C. The mercaptan component III is advantageously used in excess. Suitable solvents are ethers such as diethyl ether, diisopropyl ether, dioxane or tetrahydrofuran, halogenated hydrocarbons or aliphatic or aromatic hydrocarbons.

The compounds of the formula III are known and some of them are commercially available, or they can be prepared in analogy to known preparation processes.

The acid halides of the formula II can be obtained in a conventional manner from the 4-chloro-4,4-difluorobutyric acids of the formula IV by reaction with halogenating agents. Particularly suitable halogenating agents are $SOCl_2$, oxalyl chloride, $PCl_3$, $POCl_3$ or $PCl_5$. This is generally carried out at temperatures between $-20°$ C. and $+120°$ C., preferably between $0°$ C. and $+100°$ C. The reaction can take place without solvent or in a mixture with a solvent inert to the reaction. Examples of solvents suitable for this purpose are aromatic hydrocarbons such as benzene or toluene or halogenated hydrocarbons such as methylene chloride, chloroform or chlorobenzene. The reaction is often carried out with the addition of a catalytic amount of DMF.

The 4-chloro-4,4-difluorobutyric acids of the formula IV can be obtained from compounds of the formula V by acid or base hydrolysis.

The compounds of the formula V can be obtained by the following process:

The compounds of the formula V can be obtained by catalytic dehalogenation with hydrogen in the α position of an α-halogeno-4-chloro-4,4-difluorobutyric ester of the formula

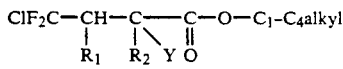

in which $R_1$ and $R_2$ have the meanings given under formula I, and Y is chlorine or bromine.

The compounds of the more restricted formula

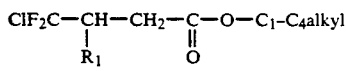

in which $R_1$ has the meaning given under formula I, can be obtained by catalytic α-dehalogenation with hydrogen from the α,α-dihalogeno-4-chloro-4,4-difluorobutyric esters of the formula

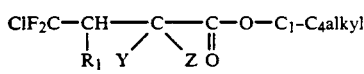

in which $R_1$ has the meaning given under formula I, and Y and Z denote, independently of one another, chlorine or bromine. The latter α,α-dihalogenobutyric esters are disclosed in EP-A-2206.

It is also possible, with suitable choice of the catalyst and of the reaction conditions, to replace the α-halogen atoms Y and Z stepwise by hydrogen.

The catalytic dehalogenation processes with the aid of hydrogen are carried out in the presence of a noble metal catalyst or Raney nickel, where appropriate in the presence of a hydrogen halide trap and of a solvent at a temperature between $0°$ C. and $+150°$ C. and under atmospheric pressure or a pressure up to 150 bar.

The compounds of the formula V can also be obtained by catalytic hydrogenation with hydrogen from the 4-chloro-4,4-difluorocrotonic acid derivatives of the formula VI

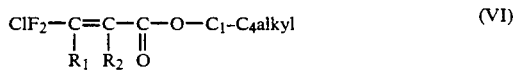

in which $R_1$ and $R_2$ have the meanings given under formula I.

The catalytic-hydrogenation of the crotonic esters of the formula VI is carried out under the conditions customary for this type of reaction. Thus, the reaction is carried out in the presence of a noble metal catalyst or of Raney nickel, preferably in an inert solvent, under a hydrogen atom atmosphere at a pressure between 1 and 150 bar.

Compounds of the formula VI in which $R_1$ and $R_2$ are hydrogen can also be obtained from compounds of the formula

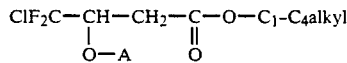

in which A is hydrogen or an acyl group, by β-elimination by known methods, for example Houben Weyl 6/1b 939 (1984). The latter compounds can be prepared from compounds of the formula

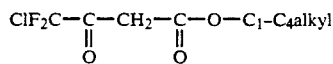

by reduction, for example catalytically with hydrogen by the method described by Reuben G. Jones in J. Amer. Chem. Soc., 70 (1948) 144. The β-ketobutyric esters used are known in some cases or can be prepared by known methods such as, for example Claisen condensation (Huang Weiynan et al.; Huaxne Xuebao 1983, 41(8) 723; C.A. 100, (1984) 22308s). Furthermore, these compounds are obtained by reacting chlorodifluoroacetyl chloride $ClF_2C-CO-Cl$ with ketene $H_2C=C=O$, and hydrolysing the resulting 4-chloro-4,4-difluoroacetoacetyl chloride of the formula

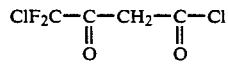

to the free acid, and converting it by reaction with the suitable alcohols into the esters. It is also possible and advantageous to obtain these esters directly by reaction of the acid chloride with an alcohol or amine. For example, a synthesis in accordance with the following scheme 1 may be regarded as advantageous for compounds of the formula V in which $R_1$ and $R_2$ are hydrogen:

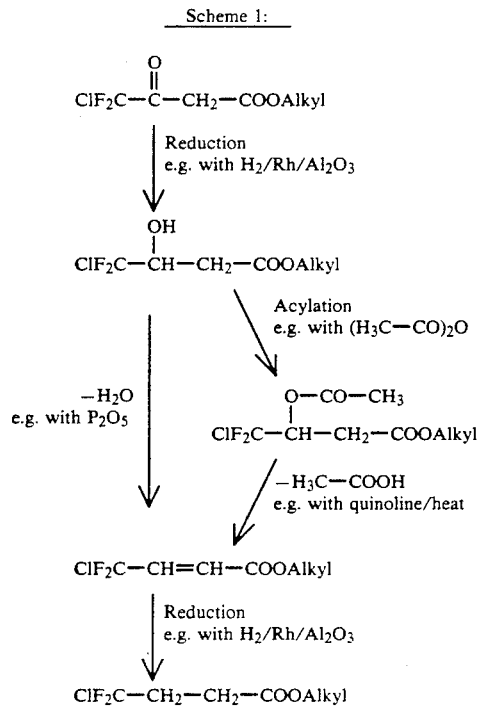

Scheme 1:

It has now been found that the compounds of the formula I according to the invention are valuable active ingredients in pest control while having favourable tolerability for warm-blooded animals, fish and plants. The use of the active ingredients according to the invention particularly relates to insects and arachnids which occur in crop and ornamental plants in agriculture, especially in cotton, vegetable and fruit plantations, in forestry, in protection of stores and materials and in the hygiene sector, especially on domestic animals and productive livestock. They are active against all or some stages of development of species of normal sensitivity, but also against those which are resistant. In this connection, their action may be displayed by direct killing of the pests or only after some time, for example at a moult, or in a reduced egg output and/or hatching rate. The abovementioned pests include: from the order Lepidoptera for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophelebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

from the order Coleoptera for example

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp. Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.; from the order of Orthoptera for example. Blatta spp., Blattella spp., Gryllotalpa spp., *Leucophaea maderae*, Locusta spp., Periplaneta spp. and Schistocerca spp.;

from the order of Isoptera for example

Reticulitermes spp.; from the order of Psocoptera for example Liposcelis spp; from the order of Anoplura for example Haematopinus spp., Linognathus spp. Pediculus spp., Pemphigus spp. and Phylloxera spp.; from the order of Mallophaga for example Damalinea spp. and Trichodectes spp.;

from the order of Thysanoptera for example

Frankliniella spp., Hercinothrips spp., Taeniothrips spp., *Thrips palmi, Thrips tabaci* and *Scirtothrips aurantii*;

from the order of Heteroptera for example

Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.;

from the order of Homoptera for example

*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum*, Trioza erytreae and Unaspis citri;

from the order of Hymenoptera for example

Acromyrmex, Atta spp., Cephus spp., Diprion spp., Diprionidae, Gilpinia polytoma, Hoplocampa spp., Lasius spp., *Monomorium pharaonis*, Neodiprion spp., Solenopsis spp. and Vespa spp.;

from the order of Diptera for example

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp. *Oscinella frit, Pegomyia hyoscyami*, Phorbia spp., *Rhagoletis pomonella*, Sciara spp., Stomoxys spp., Tabanus spp., Tannia spp. and Tipula spp.;

from the order of Siphonaptera for example

Ceratophyllus spp., Xenopsylla cheopis, from the order of Acarina for example

*Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.; and from the order of Thysanura for example

*Lepisma saccharina.*

In particular, the compounds of the formula I are suitable to a special extent for the control of pests in rice and cotton crops, such as the rice leafhoppers of the families Delphacidae and Cicadellidae, especially *Nilaparvata lugens, Laodelphax striatellus* and *Nephotettix cincticeps*, and cotton pests Heliothis and Spodoptera.

The good pesticidal action of the compounds of the formula I according to the invention corresponds to a rate of kill (mortality) of at least 50–60% of the said pests.

The action of the compounds according to the invention and of the compositions containing them can be considerably extended and adjusted to given circumstances by the addition of other insecticides and/or acaricides. Examples of suitable additives are representatives of the following classes of active ingredients: organic phosphorus compounds, nitrophenols and derivatives, formamidines, ureas, carbamates, pyrethroids, chlorinated hydrocarbons and *Bacillus thuringiensis* products.

The compounds of the formula I are employed in unmodified form or, preferably, together with the auxiliaries customary in formulation technology and can therefore be processed, for example, to emulsion concentrates, directly sprayable or dilutable solutions, diluted emulsions, wettable powders, soluble powders, dusting agents, granules, also encapsulations in polymeric substances in a known manner. The application methods, such as spraying, atomising, dusting, broadcasting or watering, are, just like the compositions, chosen to be appropriate for the intended aims and the given conditions.

The formulation, that is to say the preparations or compositions containing the active ingredient of the formula I, or combinations of these active ingredients with other insecticides or acaricides, and, where appropriate, a solid or liquid additive, are prepared in a known manner, for example by intimately mixing and/or grinding the active ingredients with extenders such as, for example, solvents, solid vehicles and, where appropriate, surface-active compounds (surfactants).

Solvents which may be suitable are: aromatic hydrocarbons, preferably the $C_8$ to $C_{12}$ fractions, such as xylene mixtures or substituted naphthalenes, phthalic esters such as dibutyl or dioctyl phthalate, aliphatic hydrocarbons such as cyclohexane, paraffins, alcohols and glycols and the ethers and esters thereof, such as ethanol, ethylene glycol, ethylene glycol monomethyl or monoethyl ether, ketones such as cyclohexanone, highly polar solvents such as N-methyl-2-pyrrolidone, dimethyl sulfoxide or dimethylformamide, and, where appropriate, epoxidised vegetable oils such as epoxidised coconut oil or soya oil, or water.

The solid vehicles which are used, for example for dusting agents and dispersible powders, as a rule are natural ground rocks such as calcite, talc, kaolin, montmorillonite or attapulgite. It is also possible to add highly disperse silicas or highly disperse absorbent polymers to improve the physical properties. Suitable particulate, adsorptive granule carriers are porous types such as pumice, crushed brick, sepiolite or bentonite, and suitable non-sorptive carrier materials are calcite or sand. It is furthermore possible to use a large number of granulated materials of an inorganic or organic nature such as, in particular, dolomite or crushed plant residues.

Suitable surface-active compounds depend on the nature of the active ingredient of the formula I to be formulated or on the combinations of these active ingredients with other insecticides or acaricides and are nonionic, cationic and/or anionic surfactants with good emulsifying, dispersing and wetting properties. By surfactants are also meant mixtures of surfactants.

Suitable anionic surfactants can be both so-called water-soluble soaps and water-soluble synthetic surface-active compounds.

Suitable soaps are the alkali metal, alkaline earth metal or optionally substituted ammonium salts of higher fatty acids ($C_{10}$–$C_{22}$), such as the sodium or potassium salts of oleic or stearic acid, or of natural mixtures of fatty acids, which can be obtained, for example, from coconut or tall oil. Further surfactants which should be mentioned are the fatty acid methyltaurine salts and modified and unmodified phospholipids.

However, it is more common to use so-called synthetic surfactants, especially fatty sulfonates, fatty sulfates, sulfonated benzimidazole derivatives or alkylarylsulfonates.

The fatty sulfonates or sulfates are usually in the form of alkali metal, alkaline earth metal or optionally substituted ammonium salts and generally have an alkyl radical having 8 to 22 C atoms, where alkyl also includes the alkyl moiety of acyl radicals, for example the sodium or calcium salt of ligninsulfonic acid, of dodecyl sulfuric ester or of a fatty alcohol sulfate mixture prepared from natural fatty acids. These also include the salts of sulfuric esters and sulfonic acids of fatty alcohol/ethylene oxide adducts. The sulfonated benzimidazole derivatives preferably contain 2 sulfo groups and one fatty acid residue having about 8–22 C atoms. Examples of alkylarylsulfonates are the sodium, calcium or triethanolamine salts of dodecylbenzenesulfonic acid, of dibutylnaphthalenesulfonic acid or of a naphthalenesulfonic acid/formaldehyde condensation product. Also suitable are appropriate phosphates such as, for example, salts of the phosphoric ester of a p-nonylphenol/(4–14)ethylene oxide adduct.

Suitable non-ionic surfactants are primarily polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon radical and 6 to 18 carbon atoms in the alkyl radical of the alkylphenols. Further suitable non-ionic surfactants are the water-soluble adducts, containing 20 to 250 ethylene glycol ether groups and 10 to 100 propylene glycol ether groups, of polyethylene oxide and polypropylene glycol, ethylenediaminopolypropylene glycol and alkylpolypropylene glycol having 1 to 10 carbon atoms in the alkyl chain. The said compounds normally contain 1 to 5 ethylene glycol units per propylene glycol unit.

Examples of non-ionic surfactants which may be mentioned are nonylphenolpolyethoxyethanols, castor oil polyglycol ethers, castor oil thioxylate, polypropylene/polyethylene oxide adducts, tributylphenoxypolyethoxyethanol, polyethylene glycol and octylphenoxypolyethoxyethanol. Also suitable are fatty acid esters of polyoxyethylenesorbitan such as polyoxyethylenesorbitan trioleate.

The cationic surfactants are, especially, quatenary ammonium salts which contain as N-substituents at least one alkyl radical having 8 to 22 C atoms and have as further substituents lower, optionally halogenated alkyl, benzyl or lower hydroxyalkyl radicals. The salts are preferably in the form of halides, methyl sulfates or ethyl sulfates, for example stearyltrimethylammonium chloride or benzyl-di-(2-chloroethyl)-ethylammonium bromide.

The surfactants customary in formulation technology are described, for example, in the following publications:

"1985 International Mc Cutcheon's Emulsifiers & Detergents", Glen Rock N.J. USA, 1985", H. Stache, "Tensid-Taschenbuch" (Surfactant Handbook), 2nd edition, C. Hanser Verlag Munich, Vienna, 1981, M. and J. Ash. "Encyclopedia of Surfactants", Vol. I–III, Chemical Publishing Co., New York, 1980–1981.

The pesticidal preparations usually contain 0.1 to 99%, in particular 0.1 to 95%, of active ingredient of the formula I or combinations of this active ingredient with other insecticides or acaricides, 1 to 99.9% of a solid or liquid additive and 0 to 25%, in particular 0.1 to 20%, of a surfactant. Whereas concentrated agents tend to be preferred as commercial product, the final user employs as a rule diluted preparations which have considerably lower concentrations of active ingredient. Typical application concentrations are between 0.1 and 1000 ppm, preferably between 0.1 and 500 ppm. The application rates per hectare are generally 1 to 1000 g of active ingredient per hectare, preferably 25 to 500 g/ha.

Particularly preferred formulations have the following compositions: (%=percent by weight)

| Emulsifiable concentrates: | |
| --- | --- |
| Active ingredient: | 1 to 20%, preferably 5 to 10% |
| Surface-active agent: | 5 to 30%, preferably 10 to 20% |
| Liquid carrier: | 50 to 94%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surface-active agent: | 1 to 40%, preferably 2 to 30% |
| Wettable powders: | |
| Active ingredient: | 0.5 to 90%, preferably 1 to 80% |
| Surface-active agent: | 0.5 to 20%, preferably 1 to 15% |
| Solid carrier material: | 5 to 95%, preferably 15 to 90% |
| Granules: | |
| Active ingredient: | 0.5 to 30%, preferably 3 to 15% |
| Solid carrier: | 99.5 to 70%, preferably 97 to 85% |

The compositions can also contain further additives such as stabilisers, foam suppressants, preservatives, viscosity regulators, binders, adhesion promoters and fertilisers or other active ingredients to achieve specific effects.

The following examples serve to illustrate the invention. They do not restrict the invention.

PREPARATION EXAMPLES

EXAMPLE P1

Ethyl 4-chloro-4,4-difluorobutyrate

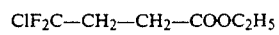

a) 22.1 g of ethyl 2,4-dichloro-4,4-difluorobutyrate are dissolved in 200 ml of absolute ethanol. 8.2 g of anhydrous sodium acetate and 2.0 g of 5% platinum/carbon catalyst are added and then gaseous hydrogen is passed in under atmospheric pressure until the hydrogen uptake is 100% of theory. The catalyst is removed by filtration and the ethanol is removed by distillation and then the remaining oil is poured onto water, and the organic phase is separated off, dried with sodium sulfate, filtered and distilled under atmospheric pressure. 14.0 g of ethyl 4-chloro-4,4-difluorobutyrate are obtained in the form of a colourless oil of boiling point 154°–156° C.

Analysis: $C_6H_9ClF_2O_2$ (186.59): Calc.: C 38.62% H 4.86% Cl 19.00% F 20.36%; Found: C 38.6% H 4.8% Cl 19.1% F 19.9%.

b) 22.1 g of ethyl 2,4-dichloro-4,4-difluorobutyrate are dissolved in 100 ml of absolute tetrahydrofuran. 10.7 g of 2,6-dimethylpyridine and 2.0 g of 5% palladium/carbon catalyst are added and then gaseous hydrogen is passed in under atmospheric pressure until the hydrogen uptake is 100% of theory. The catalyst is removed by filtration and the tetrahydrofuran is removed by distillation and then the remaining oil is poured onto water, and the organic phase is separated off, dried with sodium sulfate, filtered and distilled under atmospheric pressure. 14.0 g of ethyl 4-chloro-4,4-difluorobutyrate are obtained in the form of a colourless oil of boiling point 154°–156° C.

Analysis: $C_6H_9ClF_2O_2$ (186.59): Calc.: C 38.62% H 4.86% Cl 19.00% F 20.36%; Found: C 38.6% H 4.8% Cl 19.1% F 19.9%.

c) 25.5 g of ethyl 2,2,4-trichloro-4,4-difluorobutyrate are dissolved in 200 ml of absolute ethanol. 16.4 g of anhydrous sodium acetate and 2.0 g of 5% platinum/carbon catalyst are added and then gaseous hydrogen is passed in under atmospheric pressure until the hydrogen uptake is 2 equivalents. The catalyst is removed by filtration and the ethanol is removed by distillation and then the remaining oil is poured onto water, and the organic phase is separated off, dried with sodium sulfate, filtered and distilled under atmospheric pressure. 14.0 g of ethyl 4-chloro-4,4-difluorobutyrate are obtained in the form of a colourless oil of boiling point 154°–156° C.

Analysis: $C_6H_9ClF_2O_2$ (186.59): Calc.: C 38.62% H 4.86% Cl 19.00% F 20.36%; Found: C 38.6% H 4.8% Cl 19.1% F 19.9%.

EXAMPLE P2

4-Chloro-4,4-difluorobutyric acid

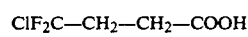

18.6 g of ethyl 4-chloro-4,4-difluorobutyrate are stirred with 100 ml of 2N-NaOH at room temperature until a homogeneous solution has been produced. The solution is then poured into 150 ml of 2N-HCl. The organic phase which has separated out is taken up in diethyl ether, dried with sodium sulfate and, after removal of the ether by distillation, distilled in vacuo. 12.6 g of 4-chloro-4,4-difluorobutyric acid are obtained in the form of a colourless oil of boiling point 88°–90° C./11 mbar.

Analysis: $C_4H_5ClF_2O_2$ (158.53): Calc.: C 30.31% H 3.18% Cl 22.36% F 23.97%: Found: C 30.3% H 3.2% Cl 22.4% F 24.2%.

EXAMPLE P3

4-Chloro-4,4-difluorobutyryl chloride

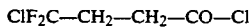

$ClF_2C-CH_2-CH_2-CO-Cl$ 15.8 g of 4-chloro-4,4-difluorobutyric acid are mixed with 50 ml of thionyl chloride and 0.2 ml of dimethylformamide and heated to +70° C. over the course of 2 hours and then maintained at +70° C. for a further 30 minutes. The reaction mixture is distilled in vacuo, and the liquid boiling at 35°–37° C./21 mbar is collected. 10.5 g of 4-chloro-4,4-difluorobutyryl chloride are obtained in the form of a clear colourless liquid.

Analysis: $C_4H_4Cl_2F_2O$ (176.98): Calc.: C 27.15% H 2.28% Cl 40.06% F 21.47%; Found: C 27.3% H 2.3% Cl 40.1% F 21.4%.

EXAMPLE P4

4-Chloro-4,4-difluorobutyric acid

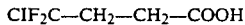

$ClF_2C-CH_2-CH_2-COOH$ 15.6 g of 4-chloro-4,4-difluorocrotonic acid are dissolved in 160 ml of tetrahydrofuran and, after addition of 0.8 g of 5% Pd/$BaSO_4$ catalyst, treated with gaseous hydrogen at room temperature and under atmospheric pressure until the hydrogen uptake is 100% of theory. The catalyst is removed by filtration and the solvent is removed by distillation and then the remaining oil is distilled in vacuo. 12 g of a colourless oil of boiling point 88°–90° C./11 mbar are obtained and are identical to the 4-chloro-4,4-difluorobutyric acid prepared in Example P2.

EXAMPLE P5

S-Benzyl 4-chloro-4,4-difluorothiobutyrate

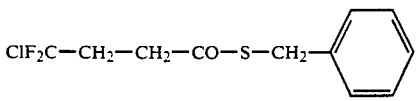

4.0 g of 4-chloro-4,4-difluorobutyric acid are added dropwise over the course of 45 minutes to a solution of 4.5 g of N,N'-carbonyldiimidazole in 30 ml of dimethylformamide at 0° C. After the solution has been stirred at 0° C. for 2 hours, 2.82 g of benzyl mercaptan are added and the mixture is allowed to warm to room temperature over the course of 17 hours. Then 100 ml of ethyl acetate are added and the organic solution is washed with saturated sodium chloride solution. The organic phase is dried over $MgSO_4$ and evaporated. The resulting crude product is purified by chromatography on silica gel (mobile phase: hexane/ethyl acetate 9:1). This results in 4.0 g of S-benzyl 4-chloro-4,4-difluorothiobutyrate as an oil, $n_D^{20}$: 1.5220.

The compounds specified in the following table are also prepared in analogy to the procedures described.

EXAMPLE P6

S-Cyclohexyl 4-chloro-4,4-difluorothiobutyrate

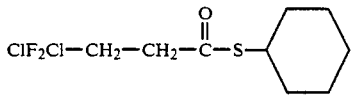

4.0 g of 4-chloro-4,4-difluorobutyryl chloride are added dropwise over the course of 30 minutes to a solution of 2.6 g of cyclohexyl mercaptan and 4.5 g of pyridine in 50 ml of toluene at 0° C. The reaction mixture is stirred at RT for 16 hours and then diluted with 150 ml of diethyl ether and subsequently washed with 50 ml each of 1N HCl, saturated $NaHCO_3$ and saturated NaCl solution. The organic phase is then dried over $MgSO_4$, filtered and evaporated. The resulting crude product is distilled at +90° C./5 mbar. 3.8 g of S-cyclohexyl 4-chloro-4,4-difluorothiobutyrate are obtained as an oil, $n_D^{23}$: 1.4748.

TABLE 1

$ClF_2C-CH_2-CH_2-CO-S-R_3$

| Comp. No. | $R_3$ | Physical data |
|---|---|---|
| 1.01 | $-CH_3$ | |
| 1.02 | $-C_2H_5$ | |
| 1.03 | $-C_3H_7$-n | $n_D^{20}$: 1.4489 |
| 1.04 | $-C_4H_9$-n | $n_D^{20}$: 1.4492 |
| 1.05 | $-C_5H_{11}$-n | |
| 1.06 | $-C_6H_{13}$-n | $n_D^{23}$: 1.4502 |
| 1.07 | $-C_9H_{19}$-n | |
| 1.08 | $-C_{12}H_{25}$-n | $n_D^{23}$: 1.4563 |
| 1.09 | $-C_{16}H_{33}$-n | |
| 1.10 | $-C_{14}H_{29}$-n | |
| 1.11 | $-C_{18}H_{37}$-n | |
| 1.12 | $-C(CH_3)_3$ | |
| 1.13 | $-C(CH_3)_2CH_2-CH_3$ | |
| 1.14 | $-CH(CH_3)_2$ | |
| 1.15 | $-CH(CH_3)-CH_2-CH_3$ | |
| 1.16 | $-CH_2-CH(CH_3)_2$ | |
| 1.17 | $-CH_2-CH(CH_3)-CH_2-CH_3$ | |
| 1.18 | $-CH_2-CH_2-CH(CH_3)_2$ | |
| 1.19 | $-CH_2COO-CH_3$ | |
| 1.20 | $-CH_2-COO-C_2H_5$ | $n_D^{23}$: 1.4551 |
| 1.21 | $-CH_2-COOCH_2-CH(C_2H_5)-(CH_2)_3CH_3$ | $n_D^{23}$: 1.4559 |

TABLE 1-continued $ClF_2C-CH_2-CH_2-CO-S-R_3$

| Comp. No. | $R_3$ | Physical data |
|---|---|---|
| 1.22 | $-CH_2-CO-NH-C_6H_5$ | |
| 1.23 | $-CH_2-CO-NHCH_3$ | |
| 1.24 | $-C(CH_3)_2-CH_2-C(CH_3)_3$ | |
| 1.25 | $-CH_2-CH_2-C_6H_5$ | |
| 1.26 | $-CH_2-CH_2-CH_2-C_6H_5$ | |
| 1.27 | $-CH_2-CH_2-CH_2-C_6H_4-Cl(4)$ | |
| 1.28 | $-CH_2-CH_2-COO-CH_3$ | |
| 1.29 | $-CH_2-CH_2-CH_2-Cl$ | |
| 1.30 | $-CH_3-CH_2-N(CH_3)_2$ | |
| 1.31 | $-CH_2-CH_2-O-COCH_3$ | |
| 1.32 | $-CH_2-CH_2-O-CH_2CH_3$ | |
| 1.33 | $-CH_2-CH_2-S-CH_2-CH_2-CH_3$ | |
| 1.34 | $-CH_2-$cyclohexyl | |
| 1.35 | $-CH_2-$cyclopropyl | |
| 1.36 | $-CH_2-C_6H_5$ | $n_D^{20}$: 1.5220 |
| 1.37 | $-CH_2-C_6H_4-Cl(2)$ | |
| 1.38 | $-CH_2-C_6H_4-Cl(4)$ | |
| 1.39 | $-CH_2-C_6H_4-CH_3(4)$ | |
| 1.40 | $-CH_2-C_6H_4-CH_3(3)$ | |
| 1.41 | $-CH_2-C_6H_4-CH_3(2)$ | |
| 1.42 | $-CH_2-C_6H_4-OCH_3(4)$ | |
| 1.43 | $-CH_2-C_6H_4-NO_2(4)$ | |
| 10.44 | $-CH_2-C_6H_4-NO_2(3)$ | |
| 1.45 | $-CH_2-C_6H_4-F(4)$ | |
| 1.46 | $-CH_2-C_6H_4-CF_3(3)$ | |
| 1.47 | $-CH_2-C_6H_4-OCF_3(4)$ | |
| 1.48 | $-CH_2-$(2,4-dichlorophenyl) | |
| 1.49 | $-CH_2-$(3,4-dichlorophenyl) | |
| 1.50 | $-CH_2-$(3,4-difluorophenyl) | |
| 1.51 | cyclohexyl | $n_D^{20}$: 1.4748 |
| 1.52 | cyclopentyl | |

TABLE 1-continued $$ClF_2C-CH_2-CH_2-CO-S-R_3$$

| Comp. No. | R₃ | Physical data |
|---|---|---|
| 1.53 | —CH₂—CH=CH—CH₃ | |
| 1.54 | —C₆H₅ | $n_D^{20}$: 1.5249 |
| 1.55 | —C₆H₄—Cl(2) | |
| 1.56 | —C₆H₄—Cl(3) | $n_D^{20}$: 1.5379 |
| 1.57 | —C₆H₄—Cl(4) | |
| 1.58 | —C₆H₄—F(4) | |
| 1.59 | —C₆H₄—Br(4) | $n_D^{23}$: 1.5531 |
| 1.60 | —C₆H₄—CH₃(4) | $n_D^{20}$: 1.5233 |
| 1.61 | —C₆H₄—OCH₃(4) | |
| 1.62 | —C₆H₄—NHCOCH₃(4) | |
| 1.63 | —C₆H₄—C(CH₃)₃(4) | |
| 1.64 | —C₆H₄—OCH₃ | |
| 1.65 | —C₆H₄—CH₃(3) | |
| 1.66 | —C₆H₄—CH₃(2) | |
| 1.67 | —C₆H₄—Br(3) | |
| 1.68 | —C₆H₄—C₂H₅(2) | |
| 1.69 | —C₆H₄—Br(2) | $n_D^{23}$: 1.5509 |
| 1.70 | —C₆H₄—OCF₃(4) | |
| 1.71 | —C₆H₄—CF₃(4) | |
| 1.72 | —C₆H₄—CF₃(3) | $n_D^{23}$: 1.4788 |
| 1.73 | 2,4-dimethylphenyl (CH₃ at 2 and 4 positions... actually 2,5-dimethylphenyl) | $n_D^{22}$: 1.518 |
| 1.74 | dimethylphenyl | $n_D^{23}$: 1.5247 |
| 1.75 | dichlorophenyl | |
| 1.76 | dichlorophenyl | |
| 1.77 | bis(trifluoromethyl)phenyl | |
| 1.78 | dichlorophenyl | |
| 1.79 | bromo-methylphenyl | |

TABLE 1-continued
ClF₂C—CH₂—CH₂—CO—S—R₃
| Comp. No. | R₃ | Physical data |
|---|---|---|
| 1.80 | 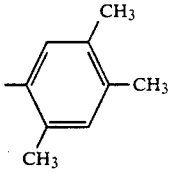 | |
| 1.81 | 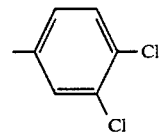 | $n_D^{23}$: 1.5523 |
| 1.82 | 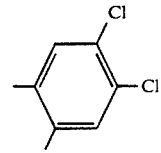 | m.p. 39–41° C. |
| 1.83 | 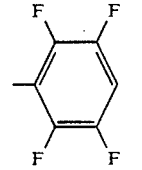 | |
| 1.84 | 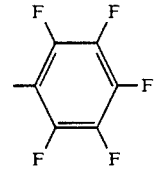 | |
| 1.85 | 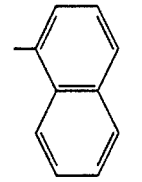 | |
| 1.86 | 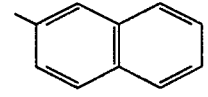 | m.p. 58–60° C. |
| 1.87 | 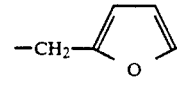 | $n_D^{20}$: 1.4930 |
| 1.88 | 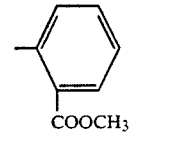 | $n_D^{23}$: 1.5297 |
| 1.89 | —CH₂—CO—O—(CH₂)₂—OCH₃ | $n_D^{23}$: 1.4600 |

TABLE 1-continued $ClF_2C-CH_2-CH_2-CO-S-R_3$

| Comp. No. | $R_3$ | Physical data |
|---|---|---|
| 1.90 | 2,6-dichlorophenyl (Cl, Cl on benzene ring) | $n_D^{23}$: 1.5222 |
| 1.91 | $-CH_2-CO-O-C_{10}H_{21}$-n | $n_D^{23}$: 1.4576 |
| 1.92 | $-CH_2-CO-O-C_{18}H_{37}$-n | m.p. 46–48° C. |
| 1.93 | $CH_2-CO-O-$cyclohexyl(H) | $n_D^{23}$: 1.4770 |
| 1.94 | $-CH_2-CO-O-C_{12}H_{25}$-n | $n_D^{24}$: 1.4580 |

FORMULATION EXAMPLES (% = percent by weight)

EXAMPLE F1

Emulsion concentrates

|  | a) | b) | c) |
|---|---|---|---|
| Active ingredient No. 1.36 | 25% | 40% | 50% |
| Calcium dodecylbenzenesulfonate | 5% | 8% | 6% |
| Castor oil polyethylene glycol ether (36 mol EO) | 5% | — | — |
| Tributylphenol polyethylene glycol ether (30 mol EO) | — | 12% | 4% |
| Cyclohexanone | — | 15% | 20% |
| Xylene mixture | 65% | 25% | 20% |

Emulsions of any desired concentration can be prepared from such concentrates by dilution with water.

EXAMPLE F2

Solutions

|  | a) | b) | c) | d) |
|---|---|---|---|---|
| Active ingredient No. 1.54 or 1.56 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling limits 160–190° C.) | — | — | 94% | — |

The solutions are suitable for application in the form of very small drops.

EXAMPLE F3

Granules

|  | a) | b) |
|---|---|---|
| Active ingredient No. 1.54 | 5% | 10% |
| Kaolin | 95% | — |
| Highly disperse silica | 1% | — |
| Attapulgite | — | 90% |

The active ingredient is dissolved in methylene chloride and sprayed onto the carrier, and the solvent is subsequently evaporated off in vacuo.

EXAMPLE F4

Dusting agent

|  | a) | b) |
|---|---|---|
| Active ingredient No. 1.60 or 1.36 | 2% | 5% |
| Highly disperse silica | 1% | 5% |
| Talc | 97% | — |
| Kaolin | — | 90% |

Dusting agents ready for use are obtained by intimately mixing the vehicles with the active ingredient.

EXAMPLE F5

Wettable powder

|  | a) | b) | c) |
|---|---|---|---|
| Active ingredient from Table 1 | 25% | 50% | 75% |
| Sodium ligninsulfonate | 5% | 5% | — |
| Sodium laurylsulfate | 3% | — | 5% |
| Sodium diisobutylnaphthalene-sulfonate | — | 6% | 10% |
| Octylphenol polyethylene glycol ether (7–8 mol EO) | — | 2% | — |
| Highly disperse silica | 5% | 10% | 10% |
| Kaolin | 62% | 27% | — |

The active ingredient is mixed with the additives and thoroughly milled in a suitable mill. Wettable powders which can be diluted with water to suspensions of any desired conentration are obtained.

EXAMPLE F6

Emulsion concentrate

| Active ingredient from Table 1 | 10% |
|---|---|
| Octylphenol polyethylene glycol ether (4–5 mol EO) | 3% |
| Calcium dodecylbenzenesulfonate | 3% |
| Castol oil polyglycol ether (36 mol EO) | 4% |
| Cyclohexanone | 30% |

-continued

| | |
|---|---|
| Xylene mixture | 50% |

Emulsions of any desired concentration can be prepared from this concentrate by dilution with water.

EXAMPLE F7

Dusting agent

| | a) | b) |
|---|---|---|
| Active ingredient from Table 1 | 5% | 8% |
| Talc | 95% | — |
| Kaolin | — | 92% |

Dusting agents ready for use are obtained by mixing the active ingredient with the carrier and milling in a suitable mill.

EXAMPLE F8

Extruder granules

| | |
|---|---|
| Active ingredient from Table 1 | 10% |
| Sodium ligninsulfonate | 2% |
| Carboxymethylcellulose | 1% |
| Kaolin | 87% |

The active ingredient is mixed with the additives, milled and moistened with water. This mixture is extruded, granulated and subsequently dried in a stream of air.

EXAMPLE F9

Coated granules

| | |
|---|---|
| Active ingredient from Table 1 | 3% |
| Polyethylene glycol (MW 200) | 3% |
| Kaolin | 94% |

The finely milled active ingredient is uniformly applied in a mixer onto the kaolin moistened with polyethylene glycol. This results in dust-free coated granules.

EXAMPLE F10

Suspension concentrate

| | |
|---|---|
| Active ingredient from Table 1 | 40% |
| Ethylene glycol | 10% |
| Nonylphenol polyethylene glycol ether (15 mol EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely milled active ingredient is intimately mixed with the additives. This results in a suspension concentrate from which suspensions of any desired concentration can be prepared by dilution with water.

BIOLOGICAL EXAMPLES

EXAMPLE B1

Action against *Boophilus microplus*

Satiated adult female ticks are stuck onto a PVC plate and covered by a wad of cotton wool. For the treatment, 10 ml of an aqueous test solution which contains 125 ppm of the active ingredient to be tested are poured over the test animals. The wad of cotton wool is then removed and the ticks are incubated for 4 weeks for egg production. The action against *Boophilus microplus* is evident either as mortality or sterility of the females or as ovicidal action on the eggs.

Compounds in Table 1 show a good action against *Boophilus microplus* in this test. An action exceeding 80% is shown, in particular, by compounds 1.03, 1.04, 1.36, 1.51, 1.54, 1.56, 1.60, 1.72, 1.73, 1.81, 1.82, 1.86, 1.87 and 1.88.

EXAMPLE B2

Ovicidal action on *Heliothis virescens*

*Heliothis virescens* eggs laid on filter paper are immersed for a short time in a test solution which contains 400 ppm of the active ingredient to be tested in acetone and water. After the test solution has dried, the eggs are incubated in Petri dishes. After 6 days, the percentage hatching of the eggs is evaluated by comparison with untreated controls (% reduction in hatching).

Compounds in Table 1 show a good action against *Heliothis virescens* in this test.

EXAMPLE B3

Action against *Aonidiella aurantii*

Potato tubers are colonised by migrating larvae ("crawlers") of *Aonidiella aurantii* (orange scale). After about 2 weeks, the potatoes are immersed in an aqueous emulsion or suspension spray liquor which contains the active ingredient to be tested in a concentration of 400 ppm. After the potato tubers treated in this way have been dried they are incubated in a plastic container. For the evaluation, the survival rate of the migrating larvae of the first filial generation of the treated scale insect population is compared 10–12 weeks later with that of the untreated controls.

Compounds in Table 1 show a good action against *Aonidiella aurantii* in this test. An action exceeding 80% is shown, in particular, by compounds 1.36, 1.54, 1.56 and 1.60.

EXAMPLE B4

Action against *Nilaparvata lugens*

Rice plants are treated with an aqueous emulsion spray liquor which contains 400 ppm of the active ingredient. After the spray deposit has dried, the rice plants are colonised by leafhopper larvae in the second and third stage. Evaluation is carried out 21 days later. The percentage reduction in the population (% action) is determined by comparing the number of surviving leafhoppers on the treated with that on the untreated plants.

Compounds in Table 1 show a good action against *Nilaparvata lugens* in this test. An action exceeding 80% is shown, in particular, by compounds 1.04, 1.36, 1.51, 1.54, 1.56, 1.60 and 1.87.

EXAMPLE B5

Action against *Tetranychus urticae*

Young bean plants are colonised by a mixed population of *Tetranychus urticae* and, 1 day later, sprayed with an aqueous emulsion spray liquor which contains 400 ppm of the active ingredient. The plants are subsequently incubated at 25° C. for 6 days and then evaluated. The percentage reduction in the population (% action) is determined by comparing the number of dead eggs, larvae and adults on the treated with that on the untreated plants.

Compounds in Table 1 show a good action against *Tetranychus urticae* in this test. An action exceeding 80% is shown, in particular, by compounds 1.36, 1.60, 1.74, 1.81, 1.82 and 1.86.

EXAMPLE B6

Ovicidal action on *Lobesia botrana*

*Lobesia botrana* eggs laid on filter paper are immersed for a short time in a test solution which contains 400 ppm of the active ingredient to be tested in acetone and water. After the test solution has dried, the eggs are incubated in Petri dishes. After 6 days the percentage hatching of the eggs is evaluated by comparing with untreated controls (% of the reduction in hatching).

Compounds in Table 1 show a good action against *Lobesia botrana* in this test.

EXAMPLE B7

Action against *Aphis craccivora*

Pea seedlings are infected with *Aphis craccivora* and subsequently sprayed with a spray liquor which contains 400 ppm of the active ingredient and incubated at 20° C. Evaluation is carried out 3 and 6 days later. The percentage reduction in the population (% action) is determined by comparing the number of dead aphids on the treated with that on the untreated plants.

Compounds in Table 1 show a good action against *Aphis craccivora* in this test. An action exceeding 80% is shown, in particular, by compounds 1.03, 1.06, 1.36, 1.51, 1.54, 1.56, 1.59, 1.60, 1.69, 1.73, 1.74, 1.81, 1.82, 1.86, 1.87, 1.88 and 1.89.

EXAMPLE B8

Systemic action against *Myzus persicae*

Pea seedlings are infected with *Myzus persicae* and subsequently placed with the roots in a spray liquor which contains 400 ppm of the active ingredient and incubated at 20° C. The evaluation is carried out 3 and 6 days later. The percentage reduction in the population (% action) is determined by comparing the number of dead aphids on the treated with that on the untreated plants.

Compounds in Table 1 show a good action against *Myzus persicae* in this test. An action exceeding 80% is shown, in particular, by compounds 1.51, 1.56, 1.60 and 1.87.

EXAMPLE B9

Systemic action against *Nilaparvata lugens*

Pots with rice plants are placed in an aqueous emulsion solution which contains 400 ppm of the active ingredient. The rice plants are subsequently colonised by larvae in the 2nd and 3rd stage. The evaluation is carried out 6 days later. The percentage reduction in the population (% action) is determined by comparing the number of leafhoppers on the treated with that on the untreated plants.

Compounds in Table 1 show a good against *Nilaparvata lugens* in this test. An action exceeding 80% is shown, in particular, by compounds 1.03, 1.04, 1.06, 1.08, 1.21, 1.36, 1.51, 1.54, 1.56, 1.59, 1.60, 1.69, 1.72, 1.73, 1.74, 1.81, 1.82, 1.86, 1.87, 1.88, 1.89 and 1.90.

EXAMPLE B10

Ovicidal action on *Adoxophyes reticulana*

*Adoxophyes reticulana* eggs laid on filter paper are immersed for a short time in a test solution which contains 400 ppm of the active ingredient to be tested in acetone and water. After the test solution has dried, the eggs are incubated in Petri dishes. After 6 days, the percentage hatching of the eggs is evaluated by comparison with untreated controls (% reduction in hatching).

Compounds in Table 1 show a good action against *Adoxophyes reticulana* in this test. An action exceeding 80% is shown, in particular, by compounds 1.03, 1.04, 1.36, 1.54 and 1.60.

EXAMPLE B11

Ovi/larvicidal action on *Heliothis virescens*

*Heliothis virescens* eggs laid on cotton are sprayed with an aqueous emulsion spray liquor which contains 400 ppm of the active ingredient. After 8 days, the percentage hatching of the eggs and the survival rates of the caterpillars are evaluated by comparison with untreated controls (% reduction in the population).

Compounds in Table 1 show a good action against *Heliothis virescens* in this test. An action exceeding 80% is shown, in particular, by compounds 1.03, 1.04, 1.06, 1.08, 1.21, 1.36, 1.51, 1.54, 1.56, 1.59, 1.60, 1.69, 1.72, 1.73, 1.74, 1.81, 1.82, 1.86, 1.87, 1.88, 1.89 and 1.90.

EXAMPLE B12

Action against *Dermanyssus gallinae*

2 to 3 ml of a solution containing 100 ppm of active ingredient and about 200 mites in various stages of development are placed in a glass container which is open at the top. The container is then closed with a wad of cotton wool, shaken for 10 minutes until the mites are completely wetted and then briefly inverted so that the remaining test solution can be absorbed by the cotton wool. The mortality of the mites is determined after 3 days.

Compounds in Table 1 show a good action against *Dermanyssus gallinae* in this test. An action exceeding 80% is shown, in particular, by compounds 1.03, 1.04, 1.36, 1.51, 1.54, 1.56 and 1.60.

EXAMPLE B13

Action against *Heliothis virescens* caterpillars

Young soya plants are sprayed with an aqueous emulsion spray liquor which contains 400 ppm of the active ingredient. After the spray deposit has dried, the soya plants are colonised with 10 caterpillars of the first stage of *Heliothis virescens* and placed in a plastic container. The evaluation is carried out 6 days later. The percentage reduction in the population or the percentage reduction in the damage (% action) was determined by comparing the number of dead caterpillars and the damage on the treated with those on the untreated plants.

Compounds in Table 1 show a good action against *Heliothis virescens* in this test. An action exceeding 80% is shown, in particular, by compounds 1.36, 1.54, 1.56 and 1.60.

EXAMPLE B14

Ovicidal action on *Cydia pomonella*

*Cydia pomonella* eggs laid on filter paper are immersed for a short time in a test solution which contains 400 ppm of the active ingredient to be tested in acetone and water. After the test solution has dried, the eggs are incubated in Petri dishes. After 6 days the percentage hatching of the eggs is evaluated by comparison with untreated controls (% reduction in hatching).

Compounds in Table 1 show a good action against *Cydia pomonella* in this test. An action exceeding 80% is shown, in particular, by compounds 1.03 and 1.04.

EXAMPLE B15

Action against *Diabrotica balteata* larvae

Maize seedlings are sprayed with an aqueous emulsion spray liquor which contains 400 ppm of the active ingredient. After the spray deposit has dried, the maize seedlings are colonised with 10 larvae of the second stage of *Diabrotica balteata* and placed in a plastic container. The evaluation is carried out 6 days later. The percentage reduction in the population (% action) is determined by comparing the number of dead larvae on the treated with that on the untreated plants.

Compounds in Table 1 show a good action against *Diabrotica balteata* in this test. An action exceeding 80% is shown, in particular, by compounds 1.60 and 1.81.

EXAMPLE B16

Action against *Bemisia tabaci*

Kidney bean plants are placed in gauze cages and colonised with adult *Bemisia tabaci* (whiteflies). After eggs have been laid all the adults are removed and, 10 days later, the plants with the nymphs thereon are treated with an aqueous emulsion spray liquor of the active ingredient to be tested (concentration 400 ppm). Evaluation of the percentage hatching compared with the untreated controls is carried out 14 days after application of the active ingredient.

Compounds in Table 1 show a good action against *Bemisia tabaci* in this test. An action exceeding 80% is shown, in particular, by compound 1.88.

EXAMPLE B17

Action against *Diabrotica balteata* eggs 20 to 50 *Diabrotica balteata* eggs laid on cloth filters are placed in a Petri dish and treated with an aqueous emulsion spray liquor which contains 400 ppm of the active ingredient. The Petri dishes are incubated at 24° C. After 7 days, the percentage hatching of the eggs is evaluated by comparison with untreated controls (% reduction in hatching).

Compounds in Table 1 show a good action against *Diabrotica balteata* in this test.

EXAMPLE B18

Action against *Bemisia tabaci* eggs

Kidney bean plants are placed in gauze cages and colonised with adult *Bemisia tabaci* (whiteflies). After eggs have been laid all the adults are removed and, 2 days later, the plants with the nymphs thereon are treated with an aqueous emulsion spray liquor of the active ingredient to be tested (concentration 400 ppm). Evaluation of the percentage hatching compared with the untreated controls is carried out 10 days after application of the active ingredient.

Compounds in Table 1 show a good action against *Bemisia tabaci* in this test.

EXAMPLE B19

Action against *Crocidolomia binotalis* caterpillars

Young cabbage plants are sprayed with an aqueous emulsion spray liquor which contains 400 ppm of the active ingredient. After the spray deposit has dried, the cabbage plants are colonised with 10 caterpillars of the third stage of *Crocidolomia binotalis* and placed in a plastic container. The evaluation is carried out 3 days later. The percentage reduction in the damage (% action) is determined by comparing the number of dead caterpillars and the damage on the treated with that on the untreated plants.

Compounds in Table 1 show a good action against *Crocidolomia binotalis* in this test. An action exceeding 80% is shown, in particular, by compound 1.36.

EXAMPLE B20

Action against *Anthonomus grandis* adults

Young cotton plants are sprayed with an aqueous emulsion spray liquor which contains 400 ppm of the active ingredient. After the spray deposit has dried, the cotton plants are colonised with 10 adults of *Anthonomus grandis* and placed in a plastic container. The evaluation is carried out 3 days later. The percentage reduction in the population and the percentage reduction in the damage (% action) are determined by comparing the number of dead beetles and the damage on the treated with that on the untreated plants.

Compounds in Table 1 show a good action against *Anthonomus grandis* in this test. An action exceeding 80% is shown, in particular, by compounds 1.03, 1.06, 1.08, 1.21, 1.59, 1.69, 1.72, 1.73, 1.74, 1.81, 1.82, 1.86, 1.87, 1.88 and 1.90.

EXAMPLE B21

Systemic action against *Nephotettix cincticeps*

Pots with rice plants are placed in an aqueous emulsion solution which contains 400 ppm of the active ingredient. The rice plants are then colonised with larvae at the 2nd and 3rd stage. The evaluation is carried out 6 days later. The percentage reduction in the population (% action) is determined by comparing the number of leafhoppers on the treated with that on the untreated plants.

Compounds in Table 1 show a good action against *Nephotettix cincticeps* in this test.

EXAMPLE 22

Action against *Ctenocephalides felis*

20 to 25 flea eggs are placed in a 50 ml cell culture bottle which is standing horizontally and into which 15 g of flea larvae nutrient medium which contains 100 ppm of the active ingredient to be tested have previously been placed. The test bottles are incubated in an incubator and 26°-27° C. and 60-70% humidity. After 21 days, the presence of adult fleas, unhatched pupae and larvae is checked.

Compounds in Table 1 show a good action against *Ctenocephalides felis* in this test. An action exceeding 80% is shown, in particular, by compounds 1.36 and 1.56.

EXAMPLE 23

Feeding action against *Ctenocephalides felis* (systematic)

20 adult fleas of the species *Ctenocephalides felis* are placed in a shallow circular cage which is closed on both sides with gauze. A vessel which is closed on the underside with a Parafilm membrane is now placed on this cage. The vessel contains blood which contains 50 ppm of the active ingredient and is heated constantly at 37° C. The fleas consume the blood through the membrane. Evaluation is carried out 24 and 48 hours after setting up. The percentage reduction in the population (% action) is determined by comparing the number of dead fleas with treated blood with those with untreated blood. 24 hours after the treatment, the blood is replaced by new, likewise treated blood.

Compounds in Table 1 show a good action against *Ctenocephalides felis* in this test.

We claim:

1. A 4-chloro-4,4-difluorothiobutyric acid derivative of the formula I

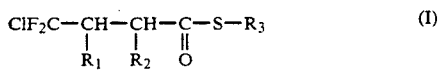

in which
R$_1$ and R$_2$ are, independently of one another, hydrogen, C$_1$-C$_4$alkyl or C$_1$-C$_4$halogenoalkyl and
R$_3$ is hydrogen C$_1$-C$_{20}$alkyl, C$_3$-C$_6$cycloalkyl, C$_3$-C$_{10}$alkenyl, aryl,
C$_3$-C$_{10}$halogenoalkenyl;
C$_3$-C$_6$cycloalkyl substituted by halogen;
aryl substituted by halogen, C$_1$-C$_4$alkyl, C$_1$-C$_4$halogenoalkyl, C$_1$-C$_4$alkoxy, C$_1$-C$_4$halogenoalkoxy,
C$_1$-C$_6$alkoxycarbonyl, C$_1$-C$_4$alkylthio or nitro; or
C$_1$-C$_{20}$alkyl substituted by halogen, di-C$_1$-C$_4$alkylamino, C$_1$-C$_4$alkoxy, C$_1$-C$_4$alkylthio, C$_1$-C$_{20}$alkoxycarbonyl, C$_3$-C$_7$cycloalkoxycarbonyl, C$_1$-C$_4$alkylcarbonyloxy, C$_3$-C$_6$cycloalkyl, aryl, C$_1$-C$_{10}$alkylaminocarbonyl or anilinocarbonyl;
where the aryl groups are in each instance selected from the group consisting of furyl, thienyl, phenyl and naphthyl and are unsubstituted or substituted by halogen, C$_1$-C$_4$alkyl, C$_1$-C$_4$halogenoalkyl, C$_1$-C$_4$alkoxy, C$_1$-C$_4$halogenoalkoxy, C$_1$-C$_4$alkylthio or nitro.

2. A compound according to claim 1, wherein R$_1$ and R$_2$ are, independently of one another, hydrogen.

3. A compound according to claim 1, wherein R$_3$ is C$_1$-C$_{20}$alkyl, C$_3$-C$_6$cycloalkyl, C$_3$-C$_{10}$alkenyl, phenyl, naphthyl, C$_3$-C$_{10}$halogenoalkenyl; C$_3$-C$_6$cycloalkyl substituted by fluorine, chlorine or bromine; phenyl substituted by fluorine, chlorine, bromine, C$_1$-C$_3$alkyl, C$_1$-C$_3$halogenoalkyl, C$_1$-C$_3$alkoxy, C$_1$-C$_3$halogenoalkoxy, C$_1$-C$_4$alkoxycarbonyl, C$_1$-C$_3$alkylthio or nitro, or C$_1$-C$_{20}$alkyl substituted by fluorine, chlorine, bromine, di-C$_1$-C$_4$alkylamino, C$_1$-C$_4$alkoxy, C$_1$-C$_4$alkylthio, C$_1$-C$_{10}$alkylcarbonyl, C$_1$-C$_{20}$alkoxycarbonyl, C$_3$-C$_7$cycloalkoxycarbonyl, C$_1$-C$_4$alkylcarbonyloxy, C$_3$-C$_6$cycloalkyl, phenyl, C$_1$-C$_{10}$alkylaminocarbonyl or anilinocarbonyl, where the phenyl groups can each be substituted by fluorine, chlorine, bromine, C$_1$-C$_3$alkyl, C$_1$-C$_3$halogenoalkyl, C$_1$-C$_3$alkoxy, C$_1$-C$_3$halogenoalkoxy, C$_1$-C$_3$alkylthio or nitro.

4. A compound according to claim 1, wherein R$_1$ and R$_2$ are, independently of one another, hydrogen, R$_3$ is phenyl, benzyl, or phenyl or benzyl in each case substituted by fluorine, chlorine, bromine, C$_1$-C$_3$alkyl, C$_1$-C$_3$halogenoalkyl, C$_1$-C$_3$alkoxy, C$_1$-C$_4$alkoxycarbonyl, C$_1$-C$_3$halogenoalkoxy, C$_1$-C$_3$alkylthio or nitro.

5. A compound according to claim 1, wherein R$_1$ and R$_2$ are, independently of one another, hydrogen, R$_3$ is C$_1$-C$_{12}$alkyl or C$_1$-C$_{12}$alkyl substituted by fluorine, chlorine, bromine, dimethylamino, methoxy, ethoxy, methylthio, ethylthio, cyclopropyl, cyclopentyl, cyclohexyl or phenyl, where the phenyl radical can in each case be substituted by fluorine, chlorine, bromine, methyl, methoxy, trifluoromethyl, trifluoromethoxy or nitro.

6. A compound according to claim 1, selected from the group consisting of
S-benzyl 4-chloro-4,4-difluorothiobutyrate
S-phenyl 4-chloro-4,4-difluorothiobutyrate
S-(4-toluyl) 4-chloro-4,4-difluorothiobutyrate and
S-(3-chlorophenyl) 4-chloro-4,4difluorothiobutyrate.

7. A pesticidal composition which contains as active component a compound of the formula I according to claim 1 and a carrier therefor.

8. A method for controlling insects and arachnids which damage animals and plants, wherein the pests or their habitat is treated with a pesticidally effective amount of a compound of said formula I according to claim 1.

* * * * *